(12) United States Patent
Chuckowree et al.

(10) Patent No.: US 8,153,639 B2
(45) Date of Patent: Apr. 10, 2012

(54) SUBSTITUTED THIENO- AND FURANO-FUSED PYRIMIDINES AS PI3K INHIBITORS

(75) Inventors: Irina S. Chuckowree, Slough (GB); Adrian J. Folkes, Slough (GB); Paul Goldsmith, Slough (GB); Timothy C. Hancox, Slough (GB); Stephen J. Shuttleworth, Slough (GB)

(73) Assignee: F. Hoffman-La Roche AG, Basel (CH)

( * ) Notice: Subject to any disclaimer, the term of this patent is extended or adjusted under 35 U.S.C. 154(b) by 614 days.

(21) Appl. No.: 12/299,600

(22) PCT Filed: May 4, 2007

(86) PCT No.: PCT/GB2007/001644
§ 371 (c)(1), (2), (4) Date: Apr. 20, 2009

(87) PCT Pub. No.: WO2007/132171
PCT Pub. Date: Nov. 22, 2007

(65) Prior Publication Data
US 2009/0209559 A1 Aug. 20, 2009

(30) Foreign Application Priority Data

May 4, 2006 (GB) .................................. 0608820.7

(51) Int. Cl.
*C07D 495/04* (2006.01)
*A61K 31/519* (2006.01)
*A61P 35/00* (2006.01)

(52) U.S. Cl. ..................................... 514/260.1; 544/278
(58) Field of Classification Search .................. 544/278; 514/260.1
See application file for complete search history.

(56) References Cited

FOREIGN PATENT DOCUMENTS

| EP | 1 277 738 | 1/2003 |
|---|---|---|
| WO | WO 99/40091 | 8/1999 |
| WO | WO 2005/014558 | 2/2005 |
| WO | WO 2006/046031 | 5/2006 |

OTHER PUBLICATIONS

"Notification of Transmittal of the International Search Report and the Written Opinion of the International Searching Authority, or the Declaration," International Application No. PCT/GB2007/001644, dated Sep. 21, 2007, pp. 1-13.

*Primary Examiner* — Susanna Moore
(74) *Attorney, Agent, or Firm* — Viksnins Harris & Padys PLLP

(57) ABSTRACT

Fused pyrimidines of formula (I):

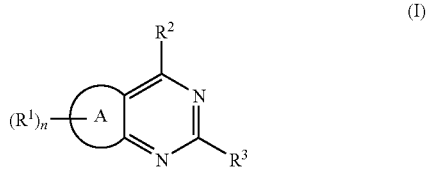

wherein A, n, $R^1$, $R^2$, and $R^3$ have any of the values defined herein and the pharmaceutically acceptable salts thereof have activity as inhibitors of PI3K and may thus be used to treat diseases and disorders arising from abnormal cell growth, function or behavior associated with PI3 kinase such as cancer, immune disorders, cardiovascular disease, viral infection, inflammation, metabolism/endocrine disorders and neurological disorders. Processes for synthesizing the compounds are also described.

17 Claims, No Drawings

SUBSTITUTED THIENO- AND FURANO-FUSED PYRIMIDINES AS PI3K INHIBITORS

Related Applications

This application is a National Stage application under 35 U.S.C. §371 and claims the benefit of priority of International Application No. PCT/GB2007/001644 having an International Filing Date of May 4, 2007 which claims the benefit of priority of United Kingdom Application Serial Number 0608820.7 filed on May 4, 2006, which are hereby incorporated by reference herein in their entirety.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

WO 01/083456 describes a series of condensed heteroaryl derivatives which have activity as inhibitors of PI3 K and which suppress cancer cell growth.

SUMMARY OF THE INVENTION

It has now been found that a novel class of fused pyrimidine compounds are effective inhibitors of PI3K with drug-like physicochemical and pharmacokinetic properties. The compounds exhibit selectivity for class Ia PI3Ks over class Ib.

Accordingly, the present invention provides a compound which is a fused pyrimidine of formula (I):

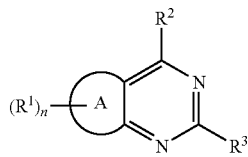

wherein
A represents a thiophene or furan ring;
n is 0, 1 or 2;
$R^1$ is a group of formula:

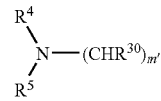

wherein
m is 0 or 1;
$R^{30}$ is H or $C_1$-$C_6$ alkyl;
$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;
$R^2$ is a heteroaryl group which contains 1, 2, 3 or 4 ring nitrogen atoms and 0, 1 or 2 additional heteroatoms selected from O, N and S, which group is monocyclic or bicyclic and which is unsubstituted or substituted;
and $R^3$ is selected from:
(a) a group of the following formula:

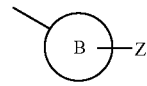

wherein B is a phenyl ring which is unsubstituted or substituted and Z is selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$, —C(O)N(R)$_2$, —NR$_2$, —NRC(O)R, —S(O)$_m$N(R)$_2$, —OC(O)R, OC(O)N(R)$_2$, —NRS(O)$_m$R, —RC(O)N(R)$_2$ CN and —NO$_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;
(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and
(c) a group comprising a benzene ring which is unsubstituted or substituted and which is fused to a heteroaryl group as defined above;
or a pharmaceutically acceptable salt thereof.

The invention further provides a compound which is a fused pyrimidine of formula (I'):

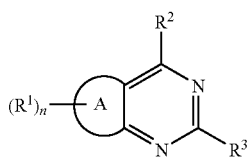

wherein
A represents a thiophene or furan ring;
n is 0, 1 or 2;
$R^1$ is a group of formula:

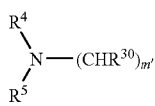

wherein
m is 0 or 1;
$R^{30}$ is H or $C_1$-$C_6$ alkyl;
$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;
$R^2$ is a heteroaryl group which contains 1, 2, 3 or 4 ring nitrogen atoms and 0, 1 or 2 additional heteroatoms selected from O, N and S, which group is monocyclic or bicyclic and which is unsubstituted or substituted;
and $R^3$ is selected from:
(a) a group of the following formula:

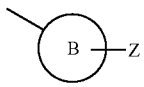

wherein B is a phenyl ring which is unsubstituted or substituted and Z is selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$, —$C(O)N(R)_2$, —$NR_2$, —$NRC(O)R$, —$S(O)_mN(R)_2$, —$OC(O)R$, $OC(O)N(R)_2$, —$NRS(O)_mR$, —$RC(O)N(R)_2$ CN, halogen and —$NO_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;
(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and
(c) a group comprising a benzene ring which is unsubstituted or substituted and which is fused to a heteroaryl group as defined above;
or a pharmaceutically acceptable salt thereof; for use as an inhibitor of PI3 kinase.

The invention also provides:
a compound which is a fused pyrimidine of formula (I') as defined above, or a pharmaceutically acceptable salt thereof, for use in treating a disease or disorder arising from abnormal cell growth, function or behaviour;
a method of treating a disease or disorder arising from abnormal cell growth, function or behaviour, which method comprises administering to a patient in need thereof a compound which is a fused pyrimidine of formula (I') as defined above, or a pharmaceutically acceptable salt thereof; and
use of a compound which is a fused pyrimidine of formula (I') as defined above, or a pharmaceutically acceptable salt thereof, in the manufacture of a medicament for treating a disease or disorder arising from abnormal cell growth, function or behaviour.

DETAILED DESCRIPTION OF THE INVENTION

The thiophene or furan ring A in formula (I) adopts either of the two available regiochemical orientations. Formula (I) thus covers regioisomers, i.e. compounds which differ by the placement of atom X in the thienopyrimidine (X=sulfur) or furopyrimidine (X=oxygen) ring system. The four possible regioisomeric forms of the ring systems encompassed by formula (I) are:

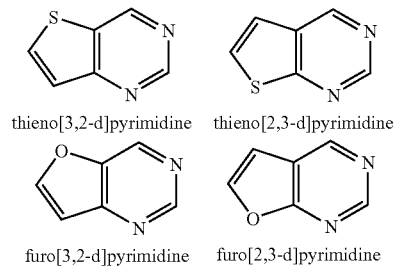

thieno[3,2-d]pyrimidine    thieno[2,3-d]pyrimidine furo[3,2-d]pyrimidine    furo[2,3-d]pyrimidine Accordingly, the present invention further provides a compound which is a fused pyrimidine of formula (Ia) or (Ib):

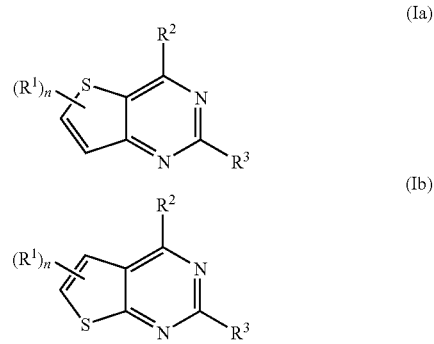

wherein each of $R^1$ to $R^3$ and n is as defined above and X is S or O.

In the compounds of the invention parameter n is typically 0, in which case the furan or thiophene ring is unsubstituted. When parameter n is 1 or 2 the group or groups $R^1$, which are the same or different in a given compound when n is 2, may be bonded to either or both of the two available ring positions on the thiophene or furan ring. Referring to structures (Ia) and (Ib) above as examples, therefore, when n is 1 the furan or thiophene ring is mono-substituted by R' at the 2-position or the 3-position. When n is 2, the thiophene or furan ring is di-substituted by R' at positions 2 and 3.

As specified herein, an alkyl group is a straight or branched chain saturated hydrocarbon radical which is unsubstituted or substituted. Typically it is $C_1$-$C_{20}$ alkyl, for instance $C_1$-$C_{10}$ alkyl, such as $C_1$-$C_6$ alkyl. $C_1$-$C_6$ alkyl is typically $C_1$-$C_4$ alkyl. It may be, for example, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), or 3,3-dimethyl-2-butyl (—$CH(CH_3)C(CH_3)_3$).

When an alkyl group is substituted it typically bears one or more substituents $R^{20}$ selected from halogen, alkoxy, carbocyclyl, a 5- or 6-membered saturated N-containing heterocyclic group as defined above, OH, SR, CN, nitro, $NR_2$, —COOR, —C(O)R, $S(O)_m R$ and —$CONR_2$, wherein each R is H, unsubstituted alkyl or $C_3$-$C_{10}$ cycloalkyl and m is 1 or 2. It is, for instance, a haloalkyl group or a group -alk-$N(R^4)(R^5)$ wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted.

Typically $R^{20}$ is selected from halogen, alkoxy, carbocyclyl, a 5- or 6-membered saturated N-containing heterocyclic group as defined above, OH, CN, $NR_2$, —COOR and —$CONR_2$, wherein each R is H or unsubstituted alkyl as defined above. It is, for instance, a haloalkyl group or a group -alk-$N(R^6)(R^5)$ wherein alk is an alkylene chain and $R^4$ and $R^5$ form, together with the N atom to which they are attached, a 5- or 6-membered saturated N-containing heterocyclic group as defined above.

An alkylene group is unsubstituted or substituted, straight or branched chain saturated divalent hydrocarbon group. Typically it is $C_1$-$C_8$ alkylene, for instance $C_1$-$C_6$ alkylene. Preferably it is $C_1$-$C_4$ alkylene, for example $C_2$-$C_4$ alkylene, such as methylene, ethylene, i-propylene, n-propylene, t-butylene, s-butylene or n-butylene. It may also be pentylene, hexylene, heptylene, octylene and the various branched chain isomers thereof. When the alkylene group is substituted it is typically substituted by a group $R^{20}$ as defined above.

An alkenyl group is an unsubstituted or substituted, straight or branched chain hydrocarbon radical having one or more double bonds. Typically it is $C_2$-$C_8$ alkenyl, for instance $C_2$-$C_6$ alkenyl, such as allyl, butenyl, butadienyl, pentenyl or hexenyl. When the alkenyl group is substituted it is typically substituted by a group $R^{20}$ as defined above or by alkyl which is unsubstituted or substituted by a group $R^{20}$ as defined above.

An alkynyl group is an unsubstituted or substituted, straight or branched chain hydrocarbon radical having one or more triple bonds. Typically it is $C_2$-$C_8$ alkynyl, for instance $C_2$-$C_6$ alkynyl, such as ethynyl, propynyl or butynyl. When the alkynyl group is substituted it is typically substituted by a group $R^{20}$ as defined above or by alkyl which is unsubstituted or substituted by a group $R^{20}$ as defined above.

A haloalkyl group is an alkyl group as defined above, substituted by one or more halogen atoms. It can be a perhaloalkyl group, for instance trifluoromethyl or perfluorohexyl.

A halogen is chlorine, fluorine, bromine or iodine. It is typically bromine or iodine.

An alkoxy group is typically $C_1$-$C_6$ alkoxy, for instance $C_1$-$C_4$ alkoxy, such as methoxy, ethoxy, i-propoxy, n-propoxy, t-butoxy, n-butoxy or s-butoxy. It is unsubstituted or substituted, for instance by a group $R^{20}$ as defined above or by alkyl which is unsubstituted or substituted by a group $R^{20}$ as defined above or by alkyl which is unsubstituted or substituted by a group $R^{20}$ as defined above. Typically it is substituted by carbocyclyl, morpholino, OH, CN, $NR_2$, —COOR or —$CONR_2$, wherein each R is H or unsubstituted alkyl as defined above.

A carbocyclyl group is a non-aromatic saturated or unsaturated monocyclic hydrocarbon ring, typically having from 3 to 10 carbon atoms, for instance 5-7 carbon atoms. It may thus be a 5-, 6- or 7-membered carbocyclyl group. It may be a $C_3$-$C_8$ cycloalkyl group, or $C_5$-$C_{10}$ cycloalkyl group, for instance cyclopropyl, cyclobutyl, cyclopentyl, cyclohexyl, cycloheptyl or cyclooctyl. Alternatively it may be a cycloalkenyl group, typically $C_4$-$C_8$ cycloalkenyl, for instance cylcopentenyl, cyclohexenyl, cyclohexadienyl, cycloheptenyl, cyclohepadienyl, cyclooctenyl or cyclooctadienyl. A carbocyclyl group may be unsubstituted or substituted, for instance by a group $R^{20}$ as defined above or by alkyl which is unsubstituted or substituted by a group $R^{20}$ as defined above. Typically it is substituted by alkoxy, morpholino, OH, CN, $NR_2$, —COOR and —$CONR_2$, wherein each R is H or unsubstituted alkyl as defined above.

A 5-, 6- or 7-membered saturated heterocyclic group may be a 5- or 6-membered saturated N-containing heterocyclic group which includes 0 or 1 additional heteroatoms selected from N, S and O, which may be fused to a benzene ring and which is unsubstituted or substituted. It is typically selected from
morpholine, piperidine, piperazine, pyrrolidine, thiomorpholine, quinoline, isoquinoline, diazepane, oxazepane and thiazepane.

When a 5- or 6-membered saturated N-containing heterocyclic group as defined above is substituted it is typically substituted by one or more substituents, for instance 1, 2 or 3 substituents, typically by 1 or 2 substituents. Typically the substituents are selected from alkyl which is unsubstituted or substituted, alkoxy which is unsubstituted or substituted, —$NR_2$, —N(R''')-alk-OR, -alk-OR, —O-alk-OR, -alk-C(O)$NR_2$, —C(O)$NR_2$, -alk-Het, —N(R)-Het, —O-Het, —N(R)—C(O)-alk-OR, —C(O)—N(R)-alk-OR, -alk-$S(O)_2R$, —N(R)-alk-OR, -alk-NR'R'', —N(R''')—$S(O)_2R$, $S(O)_2R'''$, -alk-N(R)-alk-OR, —$S(O)_2$-alk-OR, a second 5- or 6-membered saturated N-containing heterocyclic group as defined above, a 5- or 6-membered N-containing heteroaryl group which is unsubstituted or substituted and which may be fused to a benzene ring, —COOR, —$CONR_2$, oxo (=O), —$SO_2NR_2$—$SO_2$-alk-$NR_2$ and
—CO-alk-OR, wherein: alk is an alkylene chain as defined above; Het is a 5- or 6-membered N-containing heteroaryl group as defined herein which is unsubstituted or substituted; R is H or alkyl, or when two groups R are bonded to N they may form, together with the N atom, a saturated 5- or 6-membered N-containing heterocyclic group as defined herein which is unsubstituted or substituted; each of R' and R" is independently H, alkyl or alkoxy; and R''' is alkyl which is unsubstituted or substituted, for instance by $CF_3$, $NR_2$, OR, a 5- or 6-membered saturated N-containing heterocyclic group as defined herein or a 5- or 6-membered N-containing heteroaryl group as defined herein, the said heterocyclic and heteroaryl groups being unsubstituted or substituted. It may be substituted by a group $R^{20}$ as defined above or by alkyl which is unsubstituted or substituted by a group $R^{20}$ as defined above.

Typically a 5- or 6-membered saturated N-containing heterocyclic group as defined above is substituted by a group selected from alkyl which is unsubstituted or substituted, alkoxy which is unsubstituted or substituted, a second 5- or 6-membered saturated N-containing heterocyclic group as defined above, a 5- or 6-membered N-containing heteroaryl group which is unsubstituted or substituted and which may be fused to a benzene ring, —COOR, —$CONR_2$, —CONR, oxo (=O), OH, —$NSO_2R$, —$SO_2NR_2$ or —$CO(CH_2)_nOR$ wherein R is H or alkyl, —NR'R" wherein each of R' and R" is independently H, alkyl or alkoxy, and —$SO_2R'''$ wherein R''' is alkyl which is unsubstituted or substituted, for instance by $NR_2$ or a 5- or 6-membered saturated N-containing heterocyclic group as defined above.

More typically a 5- or 6-membered saturated N-containing heterocyclic group is substituted by one or more substituents selected from alkyl as defined above which is unsubstituted or substituted (for instance by $R^{20}$ as defined above), haloalkyl as defined above, alkoxy as defined above which is unsubstituted or substituted, halogen, hydroxy, CN, nitro, amino, oxo (=O), and —NR'R" wherein each of R' and R" is independently H or alkyl.

A 5-, 6- or 7-membered saturated heterocyclic group which contains 1 or 2 heteroatoms selected from N, S and O and which is unsubstituted or substituted is typically selected from tetrahydropyran, tetrahydrothiopyran, tetrahydrofuran and tetrahydrothiofuran.

When a 5-, 6- or 7-membered saturated heterocyclic group which contains 1 or 2 heteroatoms selected from N, S and O is substituted it may be substituted as specified above for a 5- or 6-membered saturated N-containing heterocyclic group.

A heteroaryl group which contains 1, 2, 3 or 4 ring nitrogen atoms and 0, 1 or 2 additional heteroatoms selected from O, N and S is monocyclic or bicyclic and is unsubstituted or substituted. It is typically a 5- to 12-membered ring. A heteroaryl group which is monocyclic is more typically a 5- to 7-membered ring, for instance a 5- or 6-membered ring. Examples of a heteroaryl group include pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Typical examples for heteroaryl in the definition of $R^2$ include pyridine, pyrimidine, imidazole and pyrazole groups. Typical examples for heteroaryl in the definition of $R^3$ include indazole, indole, pyrazole and tetrazole groups.

The heteroaryl group may be linked via any available ring carbon or heteroatom. Thus, for instance, pyrimidine may be linked as pyrimidin-1-yl, pyrimidine-2-yl, pyrimidin-3-yl or pyrimidin-4-yl. Pyridine may be linked as pyridin-1-yl, pyridine-2-yl, pyridine-3-yl or pyridine-4-yl. Pyrrole may be linked as pyrrol-1-yl, pyrrol-2-yl or pyrrol-3-yl. Imidazole may be linked as imidazol-1-yl, imidazol-2-yl, imidazol-3-yl, imidazol-4-yl or imidazol-5-yl.

Specific examples of the heteroaryl group in the definition of $R^2$ are as follows:

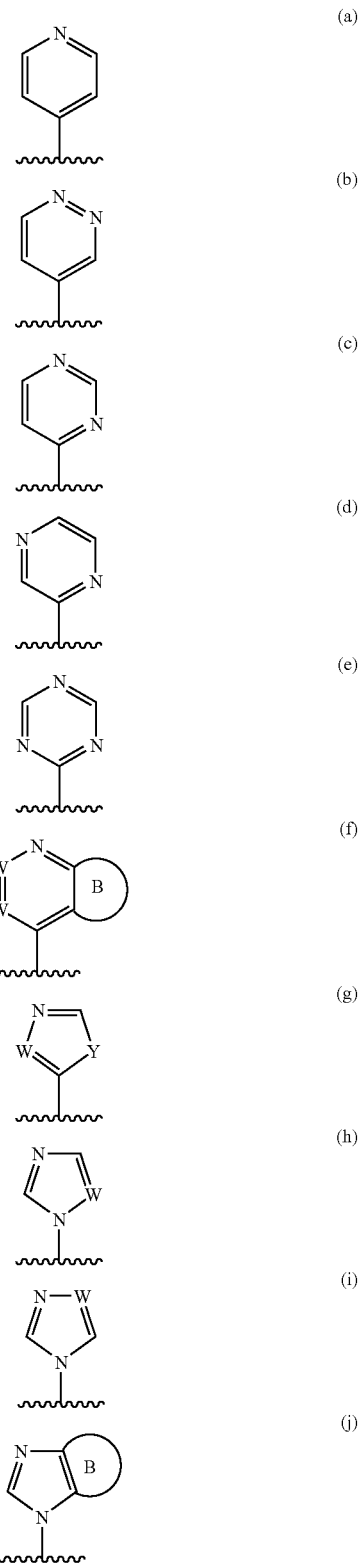

wherein:

each W is, independently, —CH or N;

Y is N, O or S; and

B is a 5-, 6- or 7-membered saturated or unsaturated carbocyclyl or heterocyclic ring.

The heteroaryl groups may be unsubstituted or substituted, for instance by a group $R^{20}$ as specified above or by alkyl which is unsubstituted or substituted by a group $R^{20}$ as defined above. Typical examples of substituents include oxo (=O), halogen, —$NR_2$, OH, CN and —$CONR_2$.

A 5- or 6-membered N containing heteroaryl group which may be fused to a benzene ring is typically selected from pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine and pyrazine. When such a heteroaryl group is substituted it may be substituted by a group $R^{20}$ as defined above or by alkyl which is unsubstituted or substituted by a group $R^{20}$ as defined above.

In $R^1$, m is 0 or 1, typically 1. $R^{30}$ is typically H. $R^4$ and $R^5$ typically form, together with the N atom to which they are attached, a saturated N-containing heterocyclic group selected from morpholine, thiomorpholine, piperidine, piperazine, pyrrolidine, quinoline, isoquinoline, diazepane, oxazepane and thiazepane. The heterocylic group formed by $R^4$ and $R^5$ is unsubstituted or substituted, for instance by the examples of substituent groups listed above, such as a group $R^{20}$ as defined above or by alkyl which is unsubstituted or substituted by a group $R^{20}$ as defined above.

In the definition (a) for $R^3$ the phenyl ring B is unsubstituted (apart from group Z) or substituted. When it is unsubstituted the group Z is the sole substituent. When it is substituted it typically comprises, in addition to group Z, one or more substituents selected from halo, alkyl, alkenyl, alkynyl, CN, $NO_2$, OR', SR', NR'$_2$, C(O)R', SOR', $SO_2$R', $SO_2$NR'$_2$, NC(O)R' and $CO_2$R', wherein each R' is independently H or $C_1$-$C_6$ alkyl.

Group Z is bonded to any available ring position on the phenyl ring B. Thus it may be situated at the 2-, 3-, 4-, 5- or 6-position of the phenyl ring. Typically it is bonded at position 3 or 4. Z is most typically other than H, such that moiety -BZ is a substituted phenyl ring. A typical example of Z is a group OR as defined above, in particular OH. In this embodiment the OR group, or OH group, is typically bonded at ring position 3 or 4 of phenyl ring B. Typically -BZ is a 3-hydroxyphenyl or 4-hydroxyphenyl group, or an isostere thereof, other than an indole or indazole group which is unsubstituted or substituted.

An isostere as used herein is a functional group which possesses binding properties which are the same as, or similar to, the 3-hydroxyphenyl or 4-hydroxyphenyl group in the context of the structure of formula (I). Isosteres of 3-hydroxyphenyl and 4-hydroxyphenyl groups are encompassed within definitions (b) and (c) above for $R^3$.

In definition (b) for $R^3$ the heteroaryl group is unsubstituted or substituted. If it is substituted it may be substituted by one or more substituents selected from a group Z, $R^{20}$ as defined above, alkyl which is unsubstituted or substituted by a $R^{20}$ as defined above, any group specified above as an additional substituent on the phenyl ring B, and an oxo group (=O). Typically, if substituted, the heteroaryl group is substituted by OH, $NH_2$ or an oxo group. In one embodiment the heteroaryl group is unsubstituted.

In definition (c) for $R^3$ the benzene ring is unsubstituted or substituted. If it is substituted it may be substituted by one or more substituents selected from a group Z, $R^{20}$ as defined above, alkyl which is unsubstituted or substituted by $R^{20}$ as defined above, and any of the groups specified above as an additional substituent on the phenyl ring B. The heteroaryl group to which the benzene ring is fused is itself unsubstituted or substituted, for instance by a group Z, $R^{20}$ or alkyl which is unsubstituted or substituted by a group $R^{20}$ as defined above; by any group specified above as an option for an additional substituent on the phenyl ring B; or by an oxo group (=O). In one embodiment both the benzene ring and the heteroaryl group are unsubstituted.

Examples of the groups included in definitions (b) and (c) for $R^3$ include indazole, indole, pyrrole, pyrazole, triazole, tetrazole, thiazole, isothiazole, oxazole, isooxazole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include indazole, indole, pyrazole and tetrazole groups. These groups may be unsubstituted or substituted, for instance by a group Z, $R^{20}$ or alkyl which is unsubstituted or substituted by a group $R^{20}$ as defined above. Typically these groups are isosteres.

More specifically, groups included in definitions (b) and (c) for $R^3$ as defined above include the following structures, which are typically isosteres as defined above:

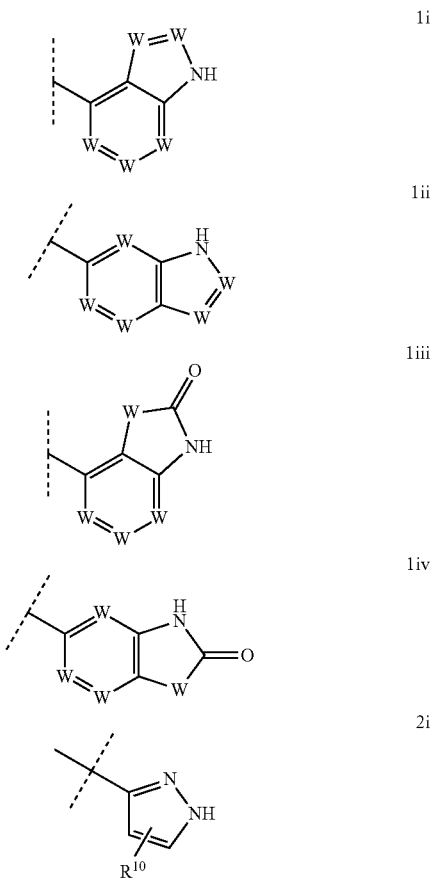

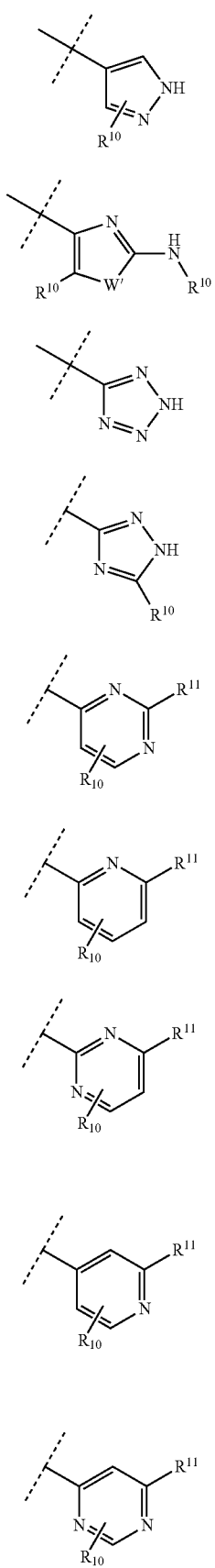
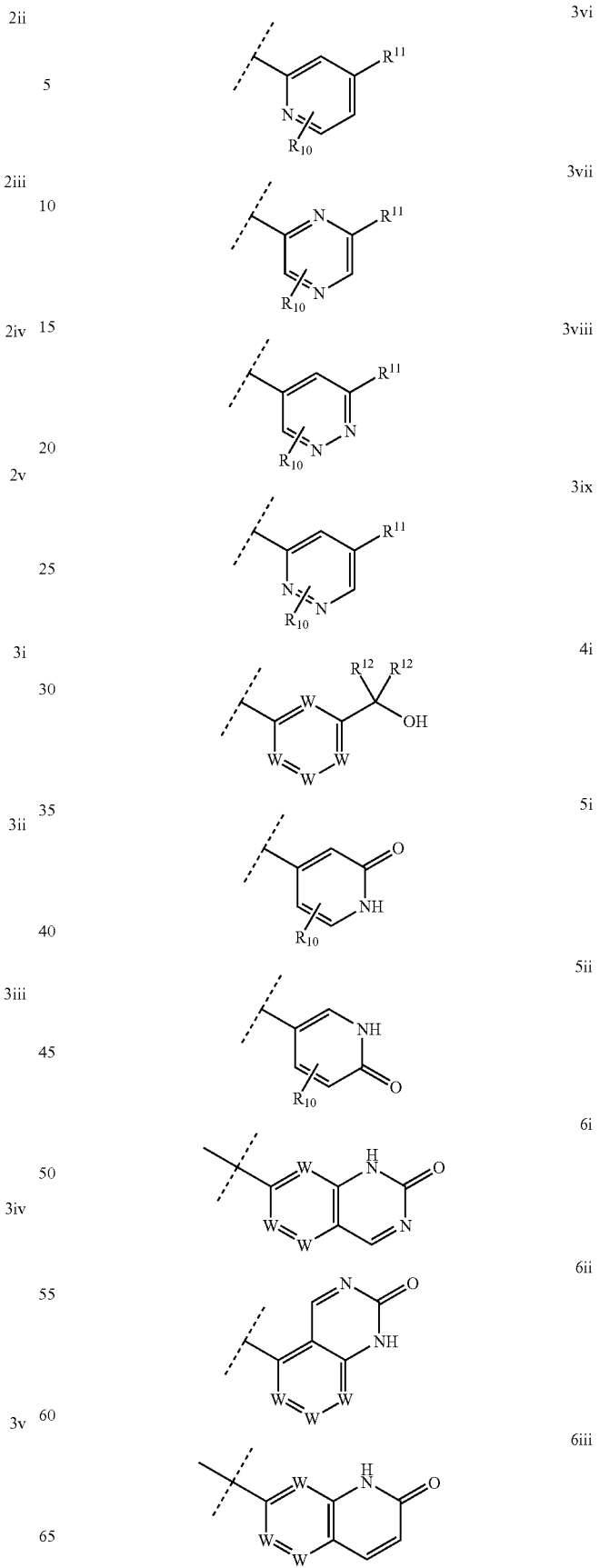

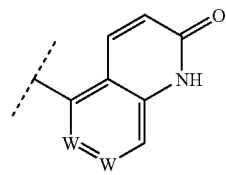

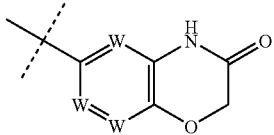

wherein each $R^{10}$ is independently selected from H, $C_1$-$C_6$ alkyl, $C_1$-$C_6$ alkoxy, $C_1$-$C_6$ acyl, —C(O)NR'R", —S(O)$_t$NR'R", aryl, heteroaryl, sulphonyl and halogen, wherein R' and R" are each independently H or $C_1$-$C_6$ alkyl and t is 1 or 2;

each $R^{11}$ is independently selected from —OR$^{10}$ and —N(R$^{10}$)$_2$, wherein $R^{10}$ is as defined above;

each $R^{12}$ is independently H, F or CF$_3$;

each W is independently selected from CR$^{10}$ and N, wherein $R^{10}$ is as defined above;

and W' is selected from O, S and NR$^{12}$ wherein $R^{12}$ is as defined above.

Specific examples of compounds of the invention include those listed in the following table:

| Compound No. | Structure | Name |
|---|---|---|
| 1 | 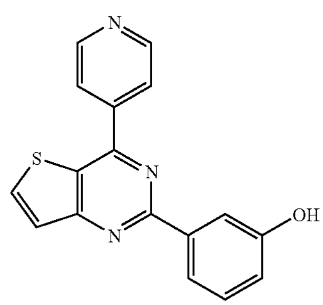 | 3-(4-Pyridin-4-yl-thieno[3,2-d]pyrimidin-2-yl)-phenol |
| 2 | 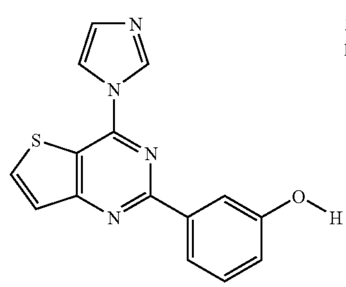 | 3-(4-Imidazol-1-yl-thieno[3,2-d]pyrimidin-2-yl)-phenol |
| 3 | 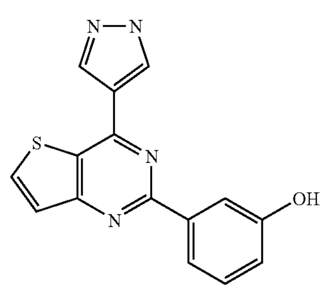 | 3-[4-(1H-Pyrazol-4-yl)-thieno[3,2-d]pyrimidin-2-yl]-phenol |

-continued

| Compound No. | Structure | Name |
|---|---|---|
| 4 | 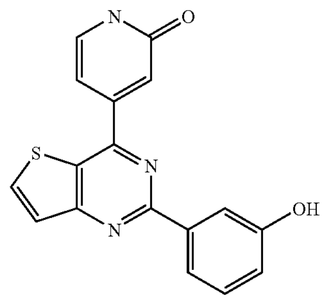 | 4-[2-(3-Hydroxy-phenyl)-thieno[3,2-d]pyrimidin-4-yl]-1H-pyridin-2-one |
| 5 | 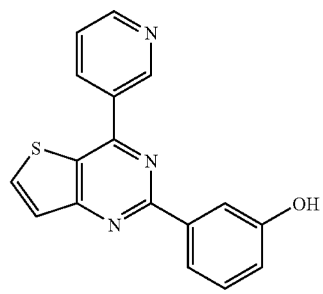 | 3-(4-Pyridin-3-yl-thieno[3,2-d]pyrimidin-2-yl)-phenol |
| 6 | 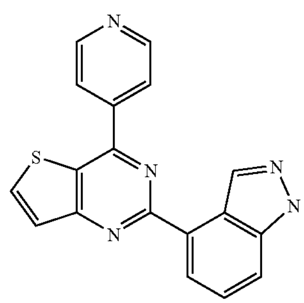 | 2-(1H-Indazol-4-yl)-4-pyridin-4-yl-thieno[3,2-d]pyrimidine |
| 7 | 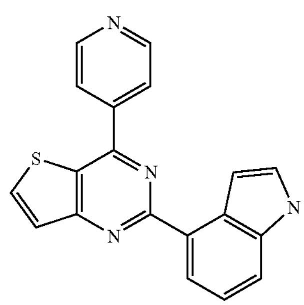 | 2-(1H-Indol-4-yl)-4-pyridin-4-yl-thieno[3,2-d]pyrimidine |
| 8 | 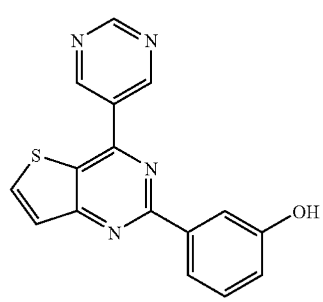 | 3-(4-Pyrimidin-5-yl-thieno[3,2-d]pyrimidin-2-yl)-phenol |

-continued

| Compound No. | Structure | Name |
|---|---|---|
| 9 | 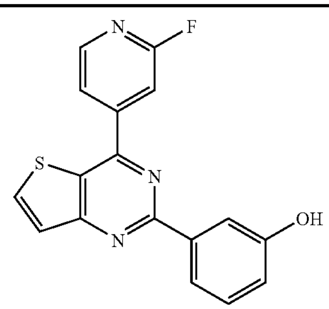 | 3-[4-(2-Fluoro-pyridin-4-yl)-thieno[3,2-d]pyrimidin-2-yl]-phenol |
| 10 | 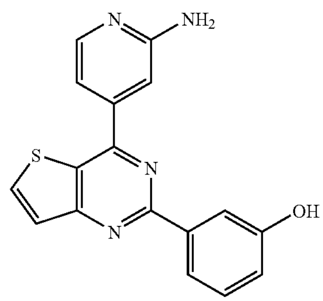 | 3-[4-(2-amino-pyridin-4-yl)-thieno[3,2-d]pyrimidin-2-yl]-phenol |
| 11 | 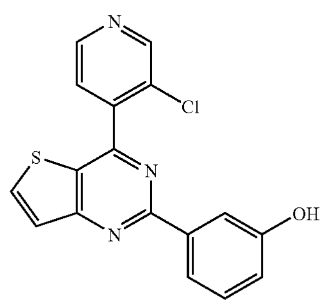 | 3-[4-(3-Chloro-pyridin-4-yl)-thieno[3,2-d]pyrimidin-2-yl]-phenol. |
| 12 | 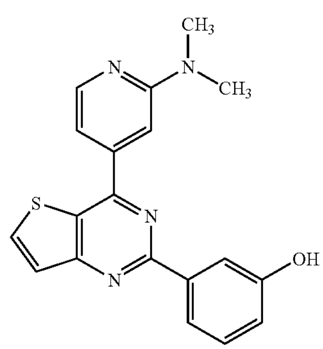 | 3-[4-(2-Dimethylamino-pyridin-4-yl)-thieno[3,2-d]pyrimidin-2-yl]-phenol |
| 13 | 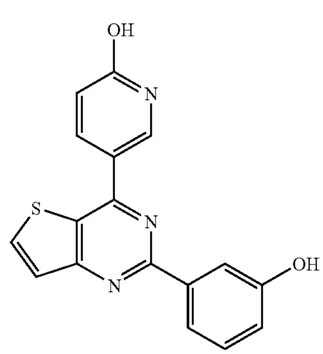 | 5-[2-(3-Hydroxy-phenyl)-thieno[3,2-d]pyrimidin-4-yl]-pyridin-2-ol |

-continued

| Compound No. | Structure | Name |
|---|---|---|
| 14 | 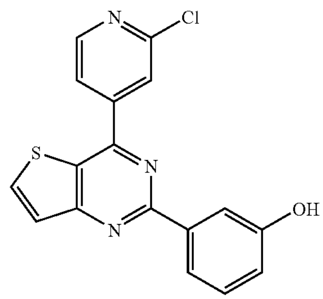 | 3-[4-(2-Chloro-pyridin-4-yl)-thieno[3,2-d]pyrimidin-2-yl]-phenol |
| 15 | 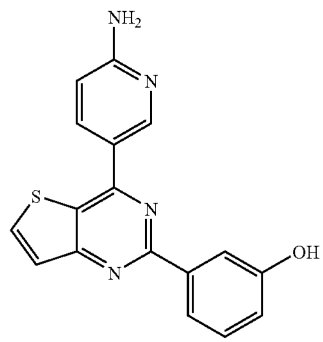 | 3-[4-(6-amino-pyridin-3-yl)-thieno[3,2-d]pyrimidin-2-yl]-phenol |
| 16 | 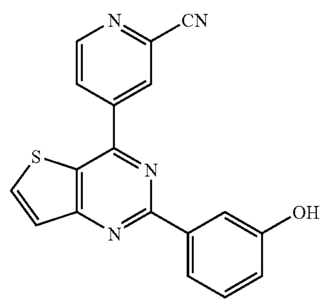 | 4-[2-(3-Hydroxy-phenyl)-thieno[3,2-d]pyrimidin-4-yl]-pyridine-2-carbonitrile |
| 17 | 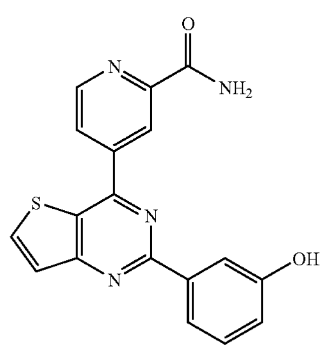 | 4-[2-(3-Hydroxy-phenyl)-thieno[3,2-d]pyrimidin-4-yl]-pyridine-2-carboxylic acid amide |
| 18 | 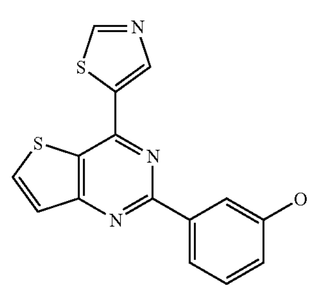 | 3-(4-Thiazol-5-yl-thieno[3,2-d]pyrimidin-2-yl)-phenol |

| Compound No. | Structure | Name |
|---|---|---|
| 19 | | 3-[4-(2-Amino-thiazol-5-yl)-thieno[3,2-d]pyrimidin-2-yl]-phenol | and the pharmaceutically acceptable salts thereof.

The compounds of formula (I) may exist in the form of geometrical isomers or tautomers depending on the kinds of substituent groups, and these isomers in separated forms or mixtures thereof may be used in the present invention. Where the compounds have asymmetric carbon atoms, optical isomer forms may exist based on such carbon atoms. All of the mixtures and the isolated forms of these optical isomers may be used in the present invention.

Compounds of the invention in which n is 0 may be produced by a process which comprises a palladium-mediated Suzuki coupling reaction as the final step. The present invention therefore provides a process for producing a fused pyrimidine of formula (I) as defined above in which n is 0, which process comprises treating a compound of formula (II):

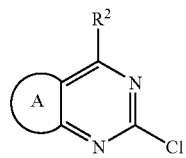
(II)

wherein A and $R^2$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

A compound of formula (II) as defined above may be produced by a process which comprises treating a compound of formula (III):

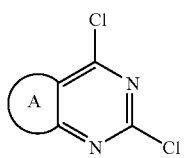
(III)

wherein A is as defined above, with a boronic acid or ester thereof of formula $R^2B(OR^{15})_2$, in which $R^2$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

A compound of formula (III) may be produced by the process described in Reference Example 1 for a compound wherein X is S, or by analogy with such a process.

Compounds of the invention in which n is 0 and $R^3$ is a 3-hydroxyphenyl group may be produced by a process which comprises treating a compound of formula (IV):

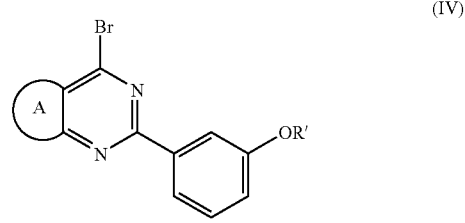
(IV)

wherein A is as defined above and R' is H or a hydroxy protecting group, with a boronic acid or ester thereof of formula $R^2B(OR^{15})_2$, in which $R^2$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

When R' is a hydroxy protecting group the process further comprises removing the protecting group by any suitable means. For instance, when the protecting group is a t-butyldimethylsilyl group, it is typically removed by treatment of the protected compound with TBAF in tetrahydrofuran.

A compound of formula (IV) may be produced by the process described in Reference Example 2 for a compound wherein X is S, or by analogy with such a process.

A suitable synthetic strategy for producing compounds of formula (I) in which n is 1 or 2 and m is 1 employs the precursor carboxaldehyde of formula (II'):

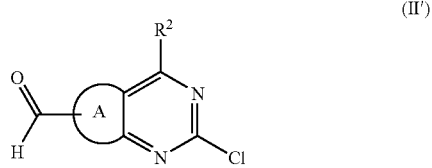
(II')

wherein A and $R^2$ are as defined above. Starting from this precursor the synthesis comprises performing, in either order, a palladium-mediated (Suzuki-type) cross-coupling reaction and a reductive amination. The present invention therefore further provides a process for producing a compound of formula (I) as defined above in which m is 1, which process comprises:

(a) treating a compound of formula (II'):

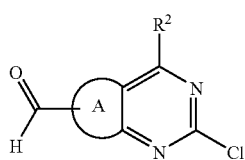

(II')

wherein A and $R^2$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (III'):

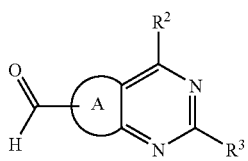

(III')

wherein A, $R^2$ and $R^3$ are as defined above, with an amine of formula $NHR^4R^5$ in which $R^4$ and $R^5$ are as defined above, in the presence of a suitable reducing agent; or (b) treating a compound of formula (II') as defined above with an amine of formula $NHR^4R^5$ wherein $R^4$ and $R^5$ are as defined above, in the presence of a suitable reducing agent; and treating the resulting compound of formula (V):

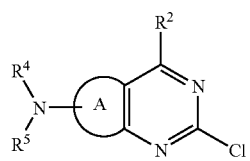

(V)

wherein A, $R^2$, $R^4$ and $R^5$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

In the processes described above both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_4$, in particular $NaBH(OAc)_3$.

The invention further provides a process for producing a compound of formula (I) in which n is 1 or 2, m is 1 and $R^3$ is a 3- or 4-hydroxyphenyl group, which process comprises:

(a) treating a compound of formula (VI):

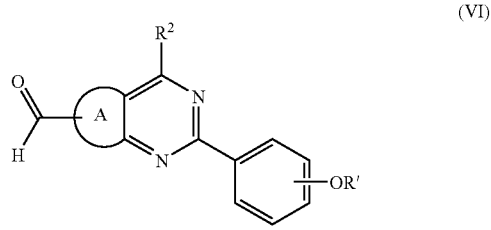

(VI)

wherein OR' is bonded at position 3 or 4 of the phenyl ring to which it is attached, R' is a hydroxy protecting group and A and $R^2$ are as defined above, with an amine of formula $NHR^4R^5$ wherein $R^4$ and $R^5$ are as defined above, in the presence of a suitable reducing agent; and (b) removing the hydroxy protecting group.

The reducing agent is typically a borohydride, for instance as specified above.

Examples of hydroxy protecting groups are known in the art, for instance as described in "Protective Groups for Organic Chemistry", Third Edition, T. W. Greene and P. G. M. Wuts, John Wiley & Sons, 1999. For instance, a hydroxy group can be protected as an acetal, a substituted acetal, an ester, a xanthate, an ether or a silyl ether. The acetal is preferably tetrahydropyran. The silyl ether is preferably trimethylsilyl ether, t-butyl dimethylsilyl ether, triiso-propylsilyl ether or t-butyldiphenyl-silyl ether. These protecting groups are removed by conventional techniques.

A compound of formula (VI) as defined above may be produced by a process which comprises treating a compound of formula (VII):

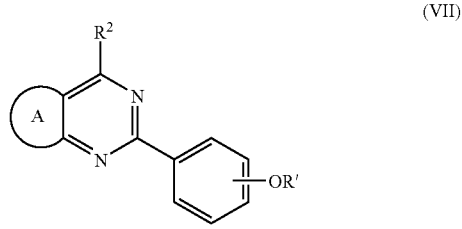

(VII)

wherein A, $R^2$ and R' are as defined above, with a lithiating agent followed by N,N'-dimethylformamide (DMF). The reaction is typically conducted by adding a solution of the lithiating agent in a non-polar organic solvent, for instance a hydrocarbon solvent such as hexane, to a suspension of the compound of formula (VI) in an organic solvent such as tetrahydrofuran (THF). If THF is used the addition takes place at a low temperature, of about −78° C. The lithiating agent is typically an alkyllithium, for instance n-butyllithium.

A compound of formula (VII) as defined above may be produced by a process which comprises treating a compound of formula (II):

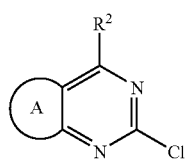

wherein A and $R^2$ are as defined above, with a boronic acid of formula (VIII):

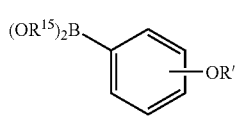

wherein R' and $R^{15}$ are as defined above, in the presence of a palladium catalyst. The reaction is conducted under conventional conditions for a Suzuki-type cross-coupling reaction, for instance as described above.

A compound of formula (I) as defined above in which n is 1 or 2 and m is 0 may be prepared by a Buchwald-type palladium-mediated nitrogen insertion reaction. Such a process may comprise treating a compound of formula (XIV):

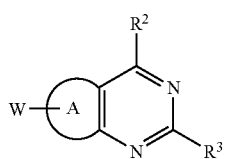

wherein A, $R^2$ and $R^3$ are as defined above and W is a halo group selected from Br and I, with an amine of formula $NHR^4R^5$ in which $R^4$ and $R^5$ are as defined above, in the presence of a palladium catalyst.

A compound of formula (XIV) may be produced by treating a compound of formula (XV):

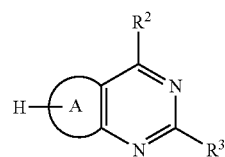

wherein A, $R^2$ and $R^3$ are as defined above, with a lithiating agent and a halogen selected from bromine and iodine. The lithiating agent is typically an alkyllithium, for instance butyllithium. The halogen is typically iodine, which gives rise to a compound of formula (XIV) in which W is I.

A compound of formula (I) as defined above in which n is 1 or 2 and m is 0 may also be prepared by an SNAr displacement reaction, for instance under the conditions described by D. Prim and G. Kirsch in Tetrahedron 55 (21), 6511-6526, 1999. Such a process comprises treating a compound of formula (XIV) as defined above in which W is Br with an amine of formula $NHR^4R^5$ in which $R^4$ and $R^5$ are as defined above in $H_2O$ under reflux for 12 hours.

A compound of formula (I) as defined above in which n is 1 or 2 and m is 0 may alternatively be prepared by treating a compound of formula (XIV) as defined above in which W is I with an amine of formula $NHR^4R^5$ in which $R^4$ and $R^5$ are as defined above in 1,4-dioxane in the presence of CuI/En and $K_3PO_4$. The reaction is conducted at about 110° C. for 24 hours. This procedure is described by Kang S-K et al in Synlett, (3), 427-430, 2002.

A pharmaceutically acceptable salt of a fused pyrimidine of the invention may be prepared using conventional techniques. Typically the process comprises treating the thienopyrimidine of formula (I) as defined above with a suitable acid in a suitable solvent. Likewise a salt may be converted into the free compound by conventional methods.

Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid. Typically the salt is a mesylate, a hydrochloride, a phosphate, a benzenesulphonate or a sulphate. Most typically the salt is a mesylate or a hydrochloride.

The salts, for instance salts with any of the inorganic or organic acids mentioned above, may be mono-salts or bis-salts. Thus, for example, the mesylate salt may be the mono-mesylate or the bis-mesylate.

The fused pyrimidines of the invention and their salts may exist as hydrates or solvates.

Compound of the present invention have been found in biological tests to be inhibitors of PI3 kinase. The compounds are typically selective for class Ia PI3 kinases over class Ib. A compound of the present invention may thus be used as an inhibitor of PI3 kinase, in particular of a class Ia PI3 kinase. Accordingly, a compound of the present invention can be used to treat a disease or disorder arising from abnormal cell growth, function or behaviour. Such abnormal cell growth, function or behaviour is typically associated with PI3 kinase. Examples of such diseases and disorders are discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity.

Examples of cancers which the present compounds can be used to treat include leukaemia, brain tumours, renal cancer, gastric cancer and cancer of the skin, bladder, breast, uterus, lung, colon, prostate, ovary and pancreas. A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of the invention as defined above and a pharmaceutically acceptable carrier, adjuvant, or vehicle, wherein said compound of the invention is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

Typically a dose to treat human patients may range from about 10 mg to about 1000 mg of a compound of the invention. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

F) Vaginally, in the form of pessaries, tampons, creams, gels, pastes, foams or spray formulations containing in addition to the active ingredient such carriers as are known in the art to be appropriate.

Sustained-release preparations of a compound of the invention may be prepared. Suitable examples of sustained-release preparations include semipermeable matrices of solid hydrophobic polymers containing a compound of Formula Ia or Ib, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate) and poly-D-(−)-3-hydroxybutyric acid.

A compound of the invention may be employed alone or in combination with other therapeutic agents for the treatment of a disease or disorder described herein, such as a hyperproliferative disorder (e.g., cancer). In certain embodiments, a compound of the invention is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of the invention such that they do not adversely affect each other. Such compounds are suitably present in combination in amounts that are effective for the purpose intended. In one embodiment, a composition of this invention comprises a compound of the invention, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The invention will be further described in the Examples which follow:

Reference Example 1

2,4-Dichloro-thieno[3,2-d]pyrimidine

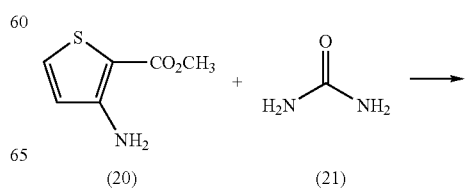

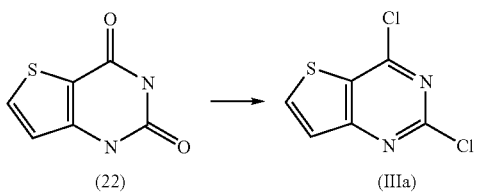

A mixture of methyl 3-amino-2-thiophenecarboxylate (20) (13.48 g, 85.85 mmol) and urea (21) (29.75 g, 5 equivalents) was heated at 190° C. for 2 hours. The hot reaction mixture was then poured onto sodium hydroxide solution and any insoluble material removed by filtration. The mixture was then acidified (HCl, 2N) to yield 1H-thieno[3,2-d]pyrimidine-2,4-dione (22) as a white precipitate which was collected by filtration and air dried (9.49 g, 66%).

A mixture of 1H-thieno[3,2-d]pyrimidine-2,4-dione (22) (9.49 g, 56.49 mmol) and phosphorous oxychloride (150 mL) was heated at reflux for 6 hours. The reaction mixture was then cooled and poured onto ice/water with vigorous stirring yielding a precipitate. The mixture was then filtered to yield 2,4-dichloro-thieno[3,2-d]pyrimidine, (IIIa), as a white solid (8.68 g, 75%).

Reference Example 2

3-(4-Bromo-thieno[3,2-d]pyrimidin-2-yl)-phenol

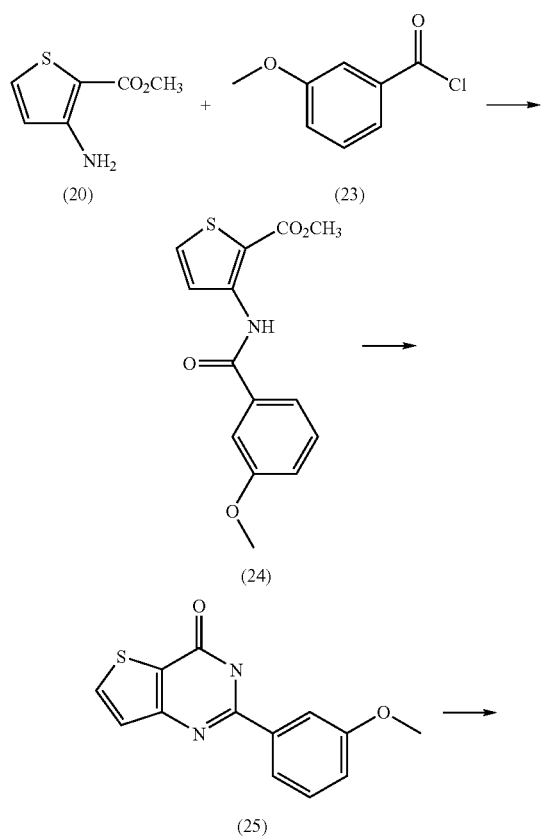

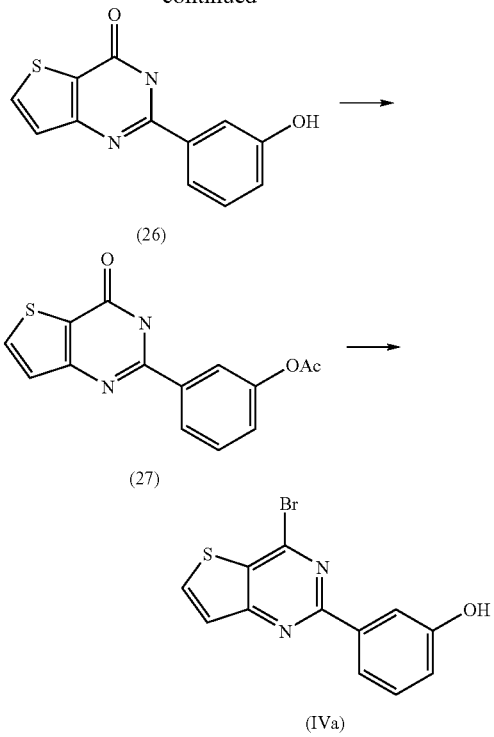

24: 3-(3-Methoxy-benzoylamino)-thiophene-2-carboxylic acid methyl ester

To a solution of methyl-3-amino-2-thiophenecarboxylate, 20, (8.0 g) in acetonitrile (100 mL) was added potassium carbonate (7.73 g) followed by m-anisoyl chloride, 23, (7.51 mL). The reaction mixture was heated to reflux, then cooled and diluted with water. 3-(3-Methoxy-benzoylamino)-thiophene-2-carboxylic acid methyl ester, 24, (12.78 g) was subsequently collected as a white solid.

$^1$H NMR (400 MHz, CDCl$_3$) 3.89 (s, 3H), 3.93 (s, 3H), 7.12 (dd, 1H, J=2.2, 8.4), 7.42 (t, 1H, J=7.9), 7.54 (d, 1H, J=5.5), 7.58 (m, 1H), 8.29 (d, 1H, J=5.5), 11.17 (brs, 1H).

25: 2-(3-Methoxy-phenyl)-3H-thieno[3,2-d]pyrimidin-4-one 3-(3-Methoxy-benzoylamino)-thiophene-2-carboxylic acid methyl ester, 24, (12.78 g) was added to methanol (200 mL) previously saturated with ammonia. The mixture was placed in a bomb reactor, and heated to 100° for 2 days. The solvent was then removed in vacuo and the resulting residue was suspended in isopropanol (250 mL); 2M sodium hydroxide solution was then added (83 mL), and the mixture was heated to reflux for 5 hours. The reaction mixture was then cooled and acidified to pH 1. 2-(3-methoxy-phenyl)-3H-thieno[3,2-d]pyrimidin-4-one, 25, (12.16 g) was collected as a white solid.

$^1$H NMR (400 MHz, d$_6$-DMSO) 3.86 (s, 3H), 7.14 (dd, 1H, J=2.2, 8.2), 7.45 (m, 2H), 7.70 (s, 1H), 7.74 (d, 1H, J=7.8), 8.22 (d, 1H, J=5.2), 12.70 (brs, 1H).

26: 2-(3-Hydroxy-phenyl)-3H-thieno[3,2-d]pyrimidin-4-one

A stirred mixture of 2-(3-methoxy-phenyl)-3H-thieno[3,2-d]pyrimidin-4-one, 25, (12.59 g, 48.7 mmol) in acetic acid (75 mL) and hydrobromic acid (75 mL of a 48% aqueous solution) was heated at reflux temperature for 3 days. The cooled reaction mixture was poured onto ice (500 ml) and stirred until all the ice had melted. The resulting precipitate was collected by filtration and dried in vacuo to give 2-(3-hydroxy-phenyl)-3H-thieno[3,2-d]pyrimidin-4-one, 26, as a grey solid (10.95 g, 92%).

$^1$H NMR (400 MHz, $d_6$-DMSO) 6.87 (m, 1H), 7.23 (t, 1H, J=8.0), 7.36 (d, 1H, J=5.2), 7.45 (m, 2H), 8.13 (d, 1H, J=5.2), 9.67 (brs, 1H), 12.52 (brs, 1H).

27: Acetic acid 3-(4-Oxo-3,4-dihydro-thieno[3,2-d]pyrimidin-2-yl)-phenyl ester A mixture of 2-(3-hydroxy-phenyl)-3H-thieno[3,2-d]pyrimidin-4-one, 26, (10.95 g, 44.8 mmol), KOAc (6.6 g, 67.2 mmol) and $Ac_2O$ (16.5 mL, 0.175 mol) in MeCN (150 mL) were heated at reflux temperature for 24 h. The cooled reaction mixture was poured onto water (500 mL) and the resulting precipitate was collected by filtration. This was then washed with water and dried to furnish acetic acid 3-(4-oxo-3,4-dihydro-thieno[3,2-d]pyrimidin-2-yl)-phenyl ester, 27, as a grey solid (10.87 g, 85%).

$^1$H NMR (400 MHz, $d_6$-DMSO) 2.32 (s, 3H), 7.36 (dd, 1H, J=2.0, 8.0), 7.47 (d, 1H, J=5.2), 7.59 (d, 1H, J=8.0), 7.93 (s, 1H), 8.04 (d, 1H, J=7.9), 8.22 (d, 1H, J=5.2), 12.75 (brs, 1H).

IVa: 3-(4-Bromo-thieno[3,2-d]pyrimidin-2-yl)-phenol

To a stirred mixture of acetic acid 3-(4-oxo-3,4-dihydro-thieno[3,2-d]pyrimidin-2-yl)-phenyl ester, 27, (1.72 g, 6.0 mmol) in MeCN (25 mL) under a nitrogen atmosphere was added $POBr_3$ (8.6 g, 30 mmol) and the resulting mixture was heated at reflux for 2.5 h. The reaction mixture was quenched by pouring onto iced water (200 mL) and the aqueous layer was neutralized by addition of solid $NaHCO_3$. The precipitate formed was collected by filtration and dried. The resulting tan solid (1.6 g) was dissolved in THF/MeOH (1:1 v/v, 20 mL). $K_2CO_3$ (1.76 g, 12.8 mmol) was added and the mixture stirred at rt for 3.5 h. The reaction mixture was diluted with $H_2O$ (20 mL), acidified to pH 3-4 with 2M HCl and extracted with EtOAc (2×100 mL). The combined organic extracts were dried ($MgSO_4$), concentrated and purified by flash chromatography (70:30 hexanes/EtOAc as eluent) to afford the title compound, IVa, as a colourless solid (0.76 g; 41%).

Reference Example 3

4-bromo-2-[3-(1,1,2,2-tetramethyl-propylsilanyloxy)-phenyl]-thieno[3,2-d]pyrimidine A hydroxy-protected derivative of compound (IVa), produced as described in Reference Example 2, was prepared as follows.

To a solution of 3-(4-bromo-thieno[3,2-d]pyrimidin-2-yl)-phenol, IVa, (240 mg) in N,N-dimethylformamide (3 mL) was added TBDMSCl (350 mg) followed by imidazole (180 mg). The reaction mixture was heated to 50° C. for 16 hours. After cooling, the mixture was diluted with water, extracted into ether, dried ($MgSO_4$) and the solvent removed in vacuo. The residue was purified using flash chromatography to yield the title compound, (278 mg).

Reference Example 4

4-(4,4,5,5-Tetramethyl-[1,3,2]dioxaborolan-2-yl)-1H-indazole

A boronic acid ester of formula $R^3B(OR^{15})_2$ in which $R^3$ is an indazole group and the two groups $OR^{15}$ together form a pinacolato group was produced by the following two synthetic strategies:

Process 1

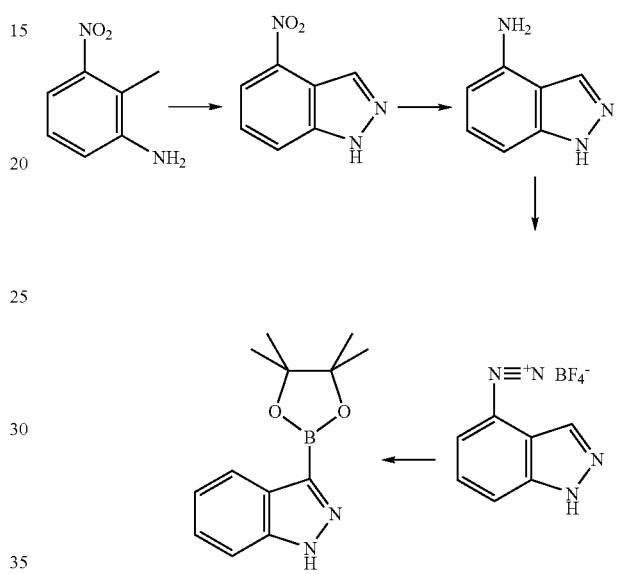

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 hours, the deep red solution was poured onto ice/water and the precipitate collected by filtration to yield 4-nitro-1H-indazole (1.98 g, 81%).

A mixture of 4-nitro-1H-indazole (760 mg, 4.68 mmol), palladium on charcoal (10%, cat.) and ethanol (30 mL) was stirred under a balloon of hydrogen for 4 hours. The reaction mixture was then filtered through celite, and the solvent removed in vacuo to yield 1H-indazol-4-ylamine (631 mg, 100%).

An aqueous solution of sodium nitrite (337 mg, 4.89 mmol) in water (2 mL) was added dropwise to a suspension of 1H-indazol-4-ylamine (631 mg, 4.74 mmol) in 6M hydrochloric acid (7.2 mL) at below 0° C. After stirring for 30 minutes sodium tetrafluorobrate (724 mg) was added. The reaction mixture became very thick and was filtered and washed briefly with water to yield 1H-indazole-4-diazonium, tetrafluoroborate salt (218 mg, 20%) as a deep red solid.

Dry methanol (4 mL) was purged with argon for 5 minutes. To this was added 1H-indazole-4-diazonium, tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 hours and then filtered through celite. The residue was purified using flash chromatography to yield the desired title compound (117 mg).

Process 2

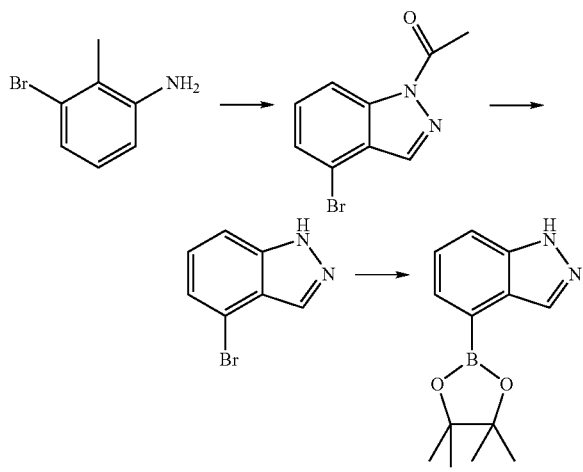

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was then added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried ($MgSO_4$).

The crude product was evaporated onto silica and purified by chromatography eluting with 20%→40% EtOAc-petrol to give 1-(4-bromo-indazol-1-yl)-ethanone (A) (3.14 g, 49%) as an orange solid, and 4-bromo-1H-indazole (B) (2.13 g, 40%) as a pale orange solid.

A $^1$H NMR (400 MHz, $CDCl_3$) 2.80 (3H, s), 7.41 (1H, t, J=7.8 Hz), 7.50 (1H, d, J=7.8 Hz), 8.15 (1H, s), 8.40 (1H, d, J=7.8 Hz).

B: $^1$H NMR (400 MHz, $CDCl_3$) 7.25 (1H, t, J=7.3 Hz), 7.33 (1H, d, J=7.3 Hz), 7.46 (1H, d, J=7.3 Hz), 8.11 (1H, s), 10.20 (1H, br s),

To a solution of the 1-(4-bromo-indazol-1-yl)-ethanone (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried ($MgSO_4$). The solvent was removed by evaporation under reduced pressure to give 4-bromo-1H-indazole (2.36 g, 93%).

To a solution of the 4-bromo-1H-indazole (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and $PdCl_2(dppf)_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried ($MgSO_4$). The crude material was purified by chromatography eluting with 30%→40% EtOAc-petrol to give an inseparable 3:1 mixture of the 4-(4,4,5,5-tetramethyl-[1,3,2]dioxaborolan-2-yl)-1H-indazole (369 mg, 60%) and indazole (60 mg, 20%); this was isolated as a yellow gum which solidified upon standing to furnish as an off-white solid.

$^1$H NMR (400 MHz, $d_6$-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s). Impurity at 1.25.

EXAMPLE 1

3-(4-Pyridin-4-yl-thieno[3,2-d]pyrimidin-2-yl)-phenol

A mixture of 4-bromo-2-[3-(1,1,2,2-tetramethyl-propylsilanyloxy)-phenyl]-thieno[3,2-d]pyrimidine, (72 mg), 4-(4,4,5,5-tetramethyl-1,3,2-dioxaborolan-2-yl)-pyridine (52 mg), sodium carbonate (57 mg), $PdCl_2(PPh_3)_2$ (0.1 eq), toluene (2 mL), ethanol (1 mL) and water (0.5 mL) was heated to 130° C. for 5 minutes under microwave irradiation. The reaction mixture was cooled, diluted with chloroform, washed with brine, dried ($MgSO_4$) and the solvent was removed in vacuo. The residue was purified using flash chromatography to yield 4-pyridin-4-yl-2-[3-(1,1,2,2-tetramethyl-propylsilanyloxy)-phenyl]-thieno[3,2-d]pyrimidine (67 mg).

The residue was dissolved in THF and tetrabutyl ammonium fluoride added (0.1M solution in THF, 0.22 mL). After 1 hour, the reaction mixture was reduced in vacuo and purified using flash chromatography to yield the title compound (1) (11 mg).

EXAMPLE 2

3-(4-Imidazol-1-yl-thieno[3,2-d]pyrimidin-2-yl)-phenol

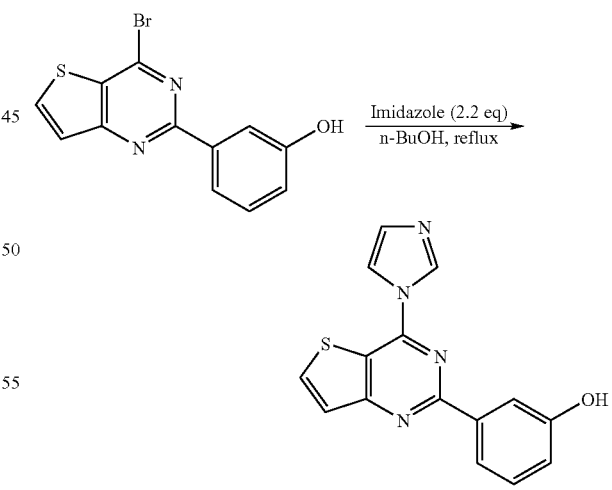

A stirred solution of 3-(4-bromo-thieno[3,2-d]pyrimidin-2-yl)-phenol (92 mg; 0.3 mmol) and imidazole (45 mg; 0.66 mmol) in n-butanol (2 ml) was heated at 105° C. for 3 days upon which time a white solid had precipitated. The solid was collected by filtration, washed with water (2 ml), MeOH (2 ml) and then dried to give the title compound (2) as a white solid (63 mg; 71%).

NMR: (DMSO): 6.95 (1H, dd, J=8.0 and 1.8), 7.34-7.38 (2H, m), 7.80 (1H, d, J=5.4), 7.99-8.02 (2H, m), 8.17 (1H, s), 8.67 (1H, d, J=5.4), 8.79 (1H, s), 9.64 (1H, br).
MS: (ESI+): MH+ 295 (38%)
$^1$H NMR (400 MHz, DMSO-d$_6$) $\delta_H$ 6.95 (1H, d, J=8.0 Hz), 7.48 (1H, t, J=8.0 Hz), 7.81 (1H, d, J=3.5 Hz), 8.04-8.07 (2H, m), 8.22 (2H, d, J=4.5 Hz), 8.63 (1H, d, J=3.5 Hz), 8.93 (2H, d, J=4.5 Hz), 9.62 (1H, s). (ESI+): MH+ 306.

EXAMPLE 3

Further Compounds of the Invention

The following compounds were prepared in the same way as the compound of Example 1, except from 3-(4-bromo-thieno[3,2-d]pyrimidin-2-yl)-phenol, using the appropriate boronic acid/boronylate ester. The final step in the preparation of the compound of Example 1, involving TBAF, was not employed in the synthesis of the compounds highlighted below.

5: 3-(4-Pyridin-3-yl-thieno[3,2-d]pyrimidin-2-yl)-phenol $^1$H NMR (400 MHz, DMSO-d$_6$) $\delta_H$ 6.92-6.95 (1H, m), 7.36 (1H, t, J=7.8 Hz), 7.72-7.75 (1H, m), 7.80 (1H, d, J=5.5 Hz), 8.03-8.05 (2H, m), 8.61-8.65 (2H, m), 8.85-8.86 (1H, m), 9.44-9.45 (1H, m), 9.61 (1H, br). (ESI+): MH+ 306.

3: 3-[4-(1H-Pyrazol-4-yl)-thieno[3,2-d]pyrimidin-2-yl]-phenol

This compound was prepared using 4-(4,4,5,5-tetramethyl-1,3,2-dioxaborolan-2-yl)-pyrazole-1-carboxylic acid tert-butyl ester; removal of the BOC protecting group was accomplished during the Suzuki cross coupling step.
$^1$H NMR (400 MHz, DMSO-d$_6$) $\delta_H$ 6.90 (1H, dd), 7.32 (1H, t, J=6.5 Hz), 7.69 (1H, d, J=5.4 Hz), 8.03-8.06 (2H, m), 8.50 (1H, d, J=5.5 Hz), 8.45-8.63 (2H, br), 9.55 (1H, br), 13.60 (1H, br). (ESI+): MH+ 295.

8: 3-(4-Pyrimidin-5-yl-thieno[3,2-d]pyrimidin-2-yl)-phenol $^1$H NMR (400 MHz, DMSO-d$_6$) $\delta_H$ 6.93-6.96 (1H, m), 7.36 (1H, t, J=8.1 Hz), 7.82 (1H, d, J=5.5 Hz), 8.04-8.06 (2H, m), 8.66 (1H, d, J=5.5 Hz), 9.47 (1H, s), 9.61 (1H, br), 9.62 (2H, s). (ESI+): MH+ 307.

9: 3-[4-(2-Fluoro-pyridin-4-yl)-thieno[3,2-d]pyrimidin-2-yl]-phenol $^1$H NMR (400 MHz, DMSO-d$_6$) $\delta_H$ 6.93-6.96 (1H, m), 7.37 (1H, t, J=8.1 Hz), 7.83 (1H, d, J=5.5 Hz), 7.94 (1H, s), 8.03-8.05 (2H, m), 8.15-8.17 (1H, m), 8.60 (1H, d, J=5.3 Hz), 8.66 (1H, d, J=5.5 Hz), 9.63 (1H, br). (ESI+): MH+ 324.

11: 3-[4-(3-Chloro-pyridin-4-yl)-thieno[3,2-d]pyrimidin-2-yl]-phenol $^1$H NMR (400 MHz, DMSO-d$_6$) $\delta_H$ 6.91-6.93 (1H, m), 7.32-7.36 (1H, m), 7.81 (1H, d, J=5.4 Hz), 7.86 (1H, d, J=4.9 Hz), 7.93-7.95 (2H, m), 8.61 (1H, d, J=5.4 Hz), 8.81 (1H, d, J=4.9 Hz), 8.96 (1H, s), 9.59 (1H, s). (ESI+): MH+ 322.

14: 3-[4-(2-Chloro-pyridin-4-yl)-thieno[3,2-d]pyrimidin-2-yl]-phenol $^1$H NMR (400 MHz, DMSO-d$_6$) $\delta_H$ 6.95 (1H, d, J=8.3 Hz), 7.38 (1H, t, J=8.1 Hz), 7.82 (1H, d, J=5.5 Hz), 8.01-8.04 (2H, m), 8.20-8.22 (1H, m), 8.26 (1H, s), 8.67 (1H, d, J=5.5 Hz), 8.78 (1H, d, J=5.2 Hz), 9.62 (1H, s). (ESI+): MH+ 340.

EXAMPLE 4

Derivatisation of Compounds of Previous Examples

The following compounds were prepared by derivatising compounds described in the previous Examples.

4: 4-[2-(3-Hydroxy-phenyl)-thieno[3,2-d]pyrimidin-4-yl]-1H-pyridin-2-one

A mixture of 3-[4-(2-fluoro-pyridin-4-yl)-thieno[3,2-d]pyrimidin-2-yl]-phenol, (60 mg), aqueous HCl (2M, 2 mL) and 1,4-dioxane (2 mL) was heated to reflux for 24 hours. Upon cooling, a precipitate formed; this was collected by filtration and washed with water and ether to yield the furnish the title compound (50 mg).
$^1$H NMR (400 MHz, DMSO-d$_6$) $\delta_H$ 6.92-6.98 (2H, m), 7.11 (1H, s), 7.36 (1H, t, J=7.8 Hz), 7.68 (1H, d, J=6.6 Hz), 7.80 (2H, 1H, d, J=5.5 Hz), 8.00-8.03 (2H, m), 8.61 (1H, d, J=5.5 Hz), 9.61 (1H, s), 12.00 (1H, br). (ESI+): MH+ 322.

13: 5-[2-(3-Hydroxy-phenyl)-thieno[3,2-d]pyrimidin-4-yl]-pyridin-2-ol

In a similar manner to 4 above, 5-[2-(3-Hydroxy-phenyl)-thieno[3,2-d]pyrimidin-4-yl]-pyridin-2-ol was prepared from 3-[4-(6-fluoro-pyridin-3-yl)-thieno[3,2-d]pyrimidin-2-yl]-phenol.
$^1$H NMR (400 MHz, DMSO-d$_6$) $\delta_H$ 6.63 (1H, d, J=9.5 Hz), 6.91 (1H, d, J=9.5 Hz), 7.35 (1H, t, J=7.9 Hz), 7.72 (1H, d, J=5.4 Hz), 7.98-8.02 (2H, m), 8.38-8.42 (2H, m), 8.53 (1H, d, J=3.5 Hz), 9.56 (1H, s), 12.20 (1H, br). (ESI+): MH+ 322.

12: 3-[4-(2-Dimethylamino-pyridin-4-yl)-thieno[3,2-d]pyrimidin-2-yl]-phenol

A mixture of 3-[4-(2-fluoro-pyridin-4-yl)-thieno[3,2-d]pyrimidin-2-yl]-phenol, (60 mg), dimethylamine hydrochloride (151 mg), triethylamine (0.31 mL) and 1,4-dioxane (3 mL) was heated to 130° C. in a sealed tube. After heating for 24 hours the reaction mixture was cooled, diluted with chloroform, washed with brine, dried (MgSO$_4$) and the solvent removed in vacuo. The residue was purified using flash chromatography to yield the title compound (40 mg).
$^1$H NMR (400 MHz, DMSO-d$_6$) $\delta_H$ 3.16 (6H, s), 6.91-6.95 (1H, m), 7.31-7.39 (3H, m), 7.79 (1H, d, J=3.5 Hz), 8.01-8.03 (2H, m), 8.38 (1H, d, J=5.5 Hz), 8.60 (1H, d, J=5.5 Hz), 9.60 (1H, s). (ESI+): MH+ 349.

15: 3-[4-(6-amino-pyridin-3-yl)-thieno[3,2-d]pyrimidin-2-yl]-phenol

In a similar manner to 12, 3-[4-(6-amino-pyridin-3-yl)-thieno[3,2-d]pyrimidin-2-yl]-phenol was prepared by treatment of 3-[4-(6-fluoro-pyridin-3-yl)-thieno[3,2-d]pyrimidin-2-yl]-phenol with aqueous ammonia in a sealed tube.
$^1$H NMR (400 MHz, DMSO-d$_6$) $\delta_H$ 6.69 (1H, d, J=8.8 Hz), 6.73 (2H, br. s), 6.91 (1H, d, J=8.5 Hz), 7.32 (1H, t, J=7.8 Hz), 7.70 (1H, d, J=5.5 Hz), 8.00-8.03 (2H, m), 8.36 (1H, dd, J=8.8 Hz, 2.5 Hz), 8.50 (1H, d, J=5.5 Hz), 8.95 (1H, d, J=2.5 Hz), 9.55 (1H, s). (ESI+): MH+ 321.

10: 3-[4-(2-amino-pyridin-4-yl)-thieno[3,2-d]pyrimidin-2-yl]-phenol

Also in a similar manner, 3-[4-(2-amino-pyridin-4-yl)-thieno[3,2-d]pyrimidin-2-yl]-phenol was prepared by treatment of 3-[4-(2-fluoro-pyridin-4-yl)-thieno[3,2-d]pyrimidin-2-yl]-phenol with aqueous ammonia in a sealed tube.

$^1$H NMR (400 MHz, DMSO-d$_6$) $\delta_H$ 6.35 (2H, br), 6.93-6.95 (1H, m), 7.25-7.28 (2H, m), 7.34-7.38 (1H, m), 7.77, (1H, d, J=5.5 Hz), 8.01-8.03 (2H, m), 8.20 (1H, d, J=5.2 Hz), 8.59 (1H, d, J=5.5 Hz), 9.61 (1H, br). (ESI+): MH+ 322.

16: 4-[2-(3-Hydroxy-phenyl)-thieno[3,2-d]pyrimidin-4-yl]-pyridine-2-carbonitrile A mixture of 3-[4-(2-chloro-pyridin-4-yl)-thieno[3,2-d]pyrimidin-2-yl]-phenol (90 mg), sodium cyanide (26 mg), nickel (II) bromide (58 mg) and NMP was heated under microwave irradiation at 200° C. for 30 minutes. The mixture was cooled, diluted with water and the precipitate collected by filtration. The title compound was isolated following flash column chromatography (31 mg).

$^1$H NMR (400 MHz, DMSO-d$_6$) $\delta_H$ 6.95 (1H, d, J=8.0 Hz), 7.38 (1H, t, J=7.8 Hz), 7.84 (1H, d, J=5.5 Hz), 8.04-8.09 (2H, m), 8.51 (1H, d, J=5.0 Hz), 8.70 (1H, d, J=5.5 Hz), 8.79 (1H, s), 9.10 (1H, d, J=5.2), 9.62 (1H, s). (ESI+): MH+ 331.

17: 4-[2-(3-Hydroxy-phenyl)-thieno[3,2-d]pyrimidin-4-yl]-pyridine-2-carboxylic acid amide A mixture of 4-[2-(3-hydroxy-phenyl)-thieno[3,2-d]pyrimidin-4-yl]-pyridine-2-carbonitrile, (48 mg), sodium hydroxide (1M, 0.3 mL) and aqueous hydrogen peroxide (30%, 0.1 mL) was stirred in methanol (3 mL) at room temperature. After stirring overnight, the reaction mixture was concentrated in vacuo, neutralised with HCl (2M), and diluted with water, yielding a precipitate. This was collected by filtration and purified using flash chromatography to yield the title compound (29 mg).

$^1$H NMR (400 MHz, DMSO-d$_6$) $\delta_H$ 6.94-6.98 (1H, m), 7.38 (1H, t, J=8.0 Hz), 7.30-7.36 (2H, m), 8.04-8.08 (2H, m), 8.30 (1H, br), 8.43 (1H, dd), 8.67 (1H, d, J=5.5 Hz), 8.87 (1H, s), 9.00 (1H, d, J=5.1 Hz), 9.69 (1H, s). (ESI+): MH+ 349.

EXAMPLE 5

Further Compounds of the Invention

The following compounds were prepared in a similar manner to compound 14, from 2-chloro-4-pyridin-4-yl-thieno[3,2-d]pyrimidine and the appropriate boronic acid/boronylate ester.

6: 2-(1H-Indazol-4-yl)-4-pyridin-4-yl-thieno[3,2-d]pyrimidine $^1$H NMR (400 MHz, MeOD, CDCl$_3$) $\delta_H$ 7.58 (1H, t, J=8.2 Hz), 7.69 (1H, d, J=8.3 Hz), 7.78 (1H, d, J=5.4 Hz), 8.12 (1H, d, J=5.4 Hz), 8.22 (2H, d, J=4.5 Hz), 8.57 (1H, d, J=7.4 Hz), 8.92 (2H, d, J=4.4 Hz), 9.21 (1H, s), 10.20 (1H, br). (ESI+): MH+ 330.

7: 2-(1H-Indol-4-yl)-4-pyridin-4-yl-thieno[3,2-d]pyrimidine $^1$H NMR (400 MHz, CDCl$_3$) $\delta_H$ 7.36-7.41 (2H, m), 7.59 (1H, d, J=7.9 Hz), 7.75-7.78 (2H, m), 8.04 (1H, d, J=5.6 Hz), 8.22 (2H, d, J=4.5 Hz), 8.35 (1H, br), 8.48 (1H, d, J=7.9 Hz), 8.92 (2H, d, J=4.5 Hz). (ESI+): MH+ 329.

EXAMPLE 6

3-(4-Thiazol-5-yl-thieno[3,2-d]pyrimidin-2-yl)-phenol (18)

A suspension of 3-(4-bromo-thieno[3,2-d]pyrimidin-2-yl)-phenol (150 mg, 0.49 mmol), 5-tributylstannanyl-thiazole (275 mg, 0.735 mmol), and Pd(PPh$_3$)$_4$ (28 mg, 0.0245 mmol) in anhydrous DMA (4 ml) was heated in a microwave at 150° C. for 15 mins. The reaction was extracted into ethyl acetate, washing with brine and water before drying the organic layer over MgSO$_4$. The crude material was purified by flash column chromatography using 1:1 ethyl acetate/petrol as the eluent. The resulting solid was triturated with dichloromethane to give the title compound as an off-white solid (22 mg, 14%).

NMR (DMSO, 400 MHz), 6.94 (1H, dd, J=1.6, 0.7), 7.37 (1H, t, J=8), 7.79 (1H, d, J=5.5), 7.97-7.99 (2H, m), 8.63 (1H, d, J=5.5), 8.87 (1H, s), 9.48 (1H, s), 9.68 (1H, s).

MS: (ESI+): MH+=312 (M+MeCN)=353

EXAMPLE 7

3-[4-(2-Amino-thiazol-5-yl)-thieno[3,2-d]pyrimidin-2-yl]-phenol (19)

A suspension of 3-(4-bromo-thieno[3,2-d]pyrimidin-2-yl)-phenol (128 mg, 0.42 mmol), (5-tributylstannyl-thiazol-2-yl)-carbamic acid tert-butyl ester (306 mg, 0.63 mmol), and Pd(PPh$_3$)$_4$ (25 mg, 0.021 mmol) in anhydrous DMA (4 ml) was heated in a microwave at 150° C. for 15 mins. The reaction was absorbed onto silica and purified using 10% methanol in ethyl acetate as the eluent to give the title compound as an off-white solid (30 mg, 22%).

NMR (DMSO, 400 MHz), 6.97 (1H, dd, J=7, 2.3), 7.38 (1H, t, J=8), 7.73 (1H, d, J=5.5), 7.96-8.0 (4H, m), 8.1 (1H, s), 8.52 (1H, d, J=5.4), 9.65 (1H, s).

MS: (ESI+): MH+=368.

EXAMPLE 8

Biological Testing

Compounds of the invention, prepared as described in the preceding Examples, were submitted to a PI3K biochemical screening assay.

Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. IC$_{50}$ values were subsequently determined using sigmoidal dose-response curve fit (variable slope). All of the compounds tested had an IC$_{50}$ against PI3K of 50 μM or less.

EXAMPLE 9

Tablet Composition

Tablets, each weighing 0.15 g and containing 25 mg of a compound of the invention are manufactured as follows:
Composition for 10,000 Tablets
Active compound (250 g)
Lactose (800 g)
Corn starch (415 g)
Talc powder (30 g)
Magnesium stearate (5 g)

The active compound, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

EXAMPLE 10

Injectable Formulation

| Formulation A | |
| --- | --- |
| Active compound | 200 mg |
| Hydrochloric Acid Solution 0.1M or Sodium Hydroxide Solution 0.1M q.s. to pH | 4.0 to 7.0 |
| Sterile water q.s. to | 10 ml |

The compound of the invention is dissolved in most of the water (35° 40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
| --- | --- |
| Active Compound | 125 mg |
| Sterile, Pyrogen-free, pH 7 Phosphate Buffer, q.s. to | 25 ml |
| Active compound | 200 mg |
| Benzyl Alcohol | 0.10 g |
| Glycofurol 75 | 1.45 g |
| Water for injection q.s to | 3.00 ml |

The active compound is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE 11

Syrup Formulation

| Active compound | 250 mg |
| --- | --- |
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A compound which is a fused pyrimidine of formula (I):

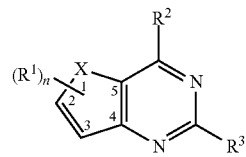

wherein
X is S;
n is 0, 1 or 2;
$R^1$ is a group of formula:

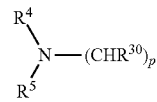

wherein
p is 0 or 1;
$R^{30}$ is H or $C_1$-$C_6$ alkyl;
$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;
$R^2$ is a heteroaryl group which contains 1, 2, 3 or 4 ring nitrogen atoms and 0, 1 or 2 additional heteroatoms selected from O, N and S, which group is monocyclic or bicyclic and which is unsubstituted or substituted;
and $R^3$ is selected from:
(a) a group of the following formula:

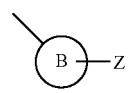

wherein B is a phenyl ring which is unsubstituted or substituted and Z is selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$ —$C(O)N(R)_2$, —$NR_2$, —$NRC(O)R$, —$S(O)_mN(R)_2$, —$OC(O)R$, $OC(O)N(R)_2$, —$NRS(O)_mR$, —$RC(O)N(R)_2$, CN and —$NO_2$, wherein each R is independently selected from H, $C_1$-$C_6$ alkyl, $C_3$-$C_{10}$ cycloalkyl and a 5-to 12-membered aryl or heteroaryl group, the group being unsubstituted or substituted, m is 1 or 2 and q is 0, 1 or 2;
(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and
(c) a group comprising a benzene ring which is unsubstituted or substituted and which is fused to a heteroaryl group as defined above;
or a pharmaceutically acceptable salt thereof.

2. A compound according to claim 1 which is selected from:
- 3-(4-Pyridin-4-yl-thieno[3,2-d]pyrimidin-2-yl)-phenol;
- 3-(4-Imidazol-1-yl-thieno[3,2-d]pyrimidin-2-yl)-phenol;
- 3-[4-(1H-Pyrazol-4-yl)-thieno[3,2-d]pyrimidin-2-yl]-phenol;
- 4-[2-(3-Hydroxy-phenyl)-thieno[3,2-d]pyrimidin-4-yl]-1H-pyridin-2-one;
- 3-(4-Pyridin-3-yl-thieno[3,2-d]pyrimidin-2-yl)-phenol;
- 2-(1H-Indazol-4-yl)-4-pyridin-4-yl-thieno[3,2-d]pyrimidine;
- 2-(1H-Indol-4-yl)-4-pyridin-4-yl-thieno[3,2-d]pyrimidine;
- 3-(4-Pyrimidin-5-yl-thieno[3,2-d]pyrimidin-2-yl)-phenol;
- 3-[4-(2-Fluoro-pyridin-4-yl)-thieno[3,2-d]pyrimidin-2-yl]-phenol;
- 3-[4-(2-amino-pyridin-4-yl)-thieno[3,2-d]pyrimidin-2-yl]-phenol;
- 3-[4-(3-Chloro-pyridin-4-yl)-thieno[3,2-d]pyrimidin-2-yl]-phenol;
- 3-[4-(2-Dimethylamino-pyridin-4-yl)-thieno[3,2-d]pyrimidin-2-yl]-phenol;
- 5-[2-(3-Hydroxy-phenyl)-thieno[3,2-d]pyrimidin-4-yl] pyridin-2-ol;
- 3-[4-(2-Chloro-pyridin-4-yl)-thieno[3,2-d]pyrimidin-2-yl]-phenol;
- 3-[4-(6-amino-pyridin-3-yl)-thieno[3,2-d]pyrimidin-2-yl]-phenol;
- 4-[2-(3-Hydroxy-phenyl)-thieno[3,2-d]pyrimidin-4-yl]-pyridine-2-carbonitrile; and
- 4-[2-(3-Hydroxy-phenyl)-thieno[3,2-d]pyrimidin-4-yl]-pyridine-2-carboxylic acid amide;
- 3-(4-Thiazol-5-yl-thieno[3,2-d]pyrimidin-2-yl)-phenol; and
- 3-[4-(2-Amino-thiazol-5-yl)-thieno[3,2-d]pyrimidin-2-yl]-phenol;

and the pharmaceutically acceptable salts of the above-mentioned free compounds.

3. A process for producing a compound as defined in claim 1 wherein n is 0, which process comprises treating a compound of formula (II):

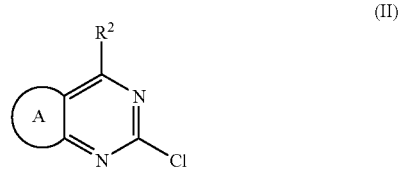

(II)

wherein A and $R^2$ are as defined in claim 1, with a boronic acid or ester thereof of formula $R^3B(OR^{15})_2$ in which $R^3$ is as defined in claim 1 and each $R^{15}$ is H or $C_1$-$C_6$ alkyl or the two groups $OR^{15}$ form, together with the boron atom to which they are attached, a pinacolato boronate ester group, in the presence of a Pd catalyst.

4. A process for producing a compound as defined in claim 1 wherein n is 0 and $R^3$ is a 3-hydroxyphenyl group, which process comprises treating a compound of formula (IV):

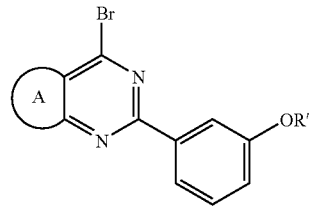

(IV)

wherein A is as defined in claim 1 and R' is H or a hydroxy protecting group, with a boronic acid or ester thereof of formula $R^2B(OR^{15})_2$, in which $R^2$ is as defined in claim 1 and each $R^{15}$ is H or $C_1$-$C_6$ alkyl or the two groups $OR^{15}$ form, together with the boron atom to which they are attached, a pinacolato boronate ester group, in the presence of a Pd catalyst.

5. A process according to claim 4 wherein R' is a protecting group, which process further comprises removing the protecting group.

6. A process for producing a pharmaceutically acceptable salt as defined in claim 1, which process comprises treating a fused pyrimidine of formula (I) as defined in claim 1 with a suitable acid in a suitable solvent.

7. A process according to claim 6, wherein the acid is selected from hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

8. A process according to claim 6, wherein the acid is selected from methanesulphonic acid, benzenesulphonic acid, hydrochloric acid, phosphoric acid and sulphuric acid.

9. A pharmaceutical composition which comprises a pharmaceutically acceptable carrier or diluent and, as an active ingredient, a compound as claimed in claim 1.

10. A composition according to claim 9 which is formulated for oral administration.

11. A process for producing a pharmaceutical composition which process comprises combining a compound as defined in claim 1 with a pharmaceutically acceptable carrier.

12. A kit comprising:
   (a) a first pharmaceutical composition comprising a compound of formula (I) as defined in claim 1; and
   (b) instructions for use.

13. A kit according to claim 12, further comprising (c) a second pharmaceutical composition, wherein the second pharmaceutical composition comprises a second compound having anti-hyperproliferative activity.

14. A kit according to claim 13 further comprising instructions for the simultaneous, sequential or separate administration of said first and second pharmaceutical compositions to a patient in need thereof.

15. A kit according to claim 13, wherein said first and second pharmaceutical compositions are contained in separate containers.

16. A kit according to claim 13, wherein said first and second pharmaceutical compositions are contained in the same container.

17. A product comprising
   (a) a compound of formula (I) as defined in claim 1; and
   (b) a compound having anti-hyperproliferative activity;
   for separate, simultaneous or sequential administration to a patient in need thereof.

* * * * *